United States Patent
Shim et al.

(10) Patent No.: US 8,600,705 B2
(45) Date of Patent: Dec. 3, 2013

(54) METHOD AND APPARATUS FOR MEASURING INTERNAL QUANTUM WELL EFFICIENCY OF LED

(75) Inventors: Jong-In Shim, Seoul (KR); Hyunsung Kim, Seoul (KR)

(73) Assignee: Industry-University Cooperation Foundation Hanyang University (KR)

( * ) Notice: Subject to any disclaimer, the term of this patent is extended or adjusted under 35 U.S.C. 154(b) by 428 days.

(21) Appl. No.: 12/905,876

(22) Filed: Oct. 15, 2010

(65) Prior Publication Data

US 2011/0178770 A1     Jul. 21, 2011

(30) Foreign Application Priority Data

Jan. 15, 2010 (KR) ........................ 10-2010-0003836

(51) Int. Cl.
*G06F 3/023* (2006.01)
*G06F 3/01* (2006.01)
*G06F 3/06* (2006.01)
*G06F 3/14* (2006.01)

(52) U.S. Cl.
USPC ............ 702/182; 702/179; 702/183; 702/189

(58) Field of Classification Search
USPC ............ 702/58, 64, 167, 179, 182, 183, 189; 252/301.4; 362/97.3; 372/39
See application file for complete search history.

(56) References Cited

U.S. PATENT DOCUMENTS

| | | | |
|---|---|---|---|
| 8,277,687 B2 * | 10/2012 | Takahashi et al. | 252/301.4 H |
| 2004/0076200 A1 * | 4/2004 | Manico et al. | 372/39 |
| 2010/0142189 A1 * | 6/2010 | Hong et al. | 362/97.3 |

FOREIGN PATENT DOCUMENTS

| | | |
|---|---|---|
| JP | 2002-107268 | 4/2002 |
| JP | 2006-125940 | 5/2006 |
| JP | 2007-088389 | 4/2007 |
| KR | 10-2009-0057225 A | 6/2009 |

OTHER PUBLICATIONS

G.B. Ren, et al., "Non-radiative recombination and efficiency of InGaN quantum well light emitting diodes", Proceedings of SPIE (2001), pp. 78-84, vol. 4283, SPIE, United States.

Satoshi Watanabe, et al., "Internal quantum efficiency of highly-efficient InxGa1-xN-based near-ultraviolet light-emitting diodes", Applied Physics Letters (Dec. 15, 2003), pp. 4906-4908, vol. 83, American Institute of Physics, United States.

J. -B. Wang, et al., "Determination and improvement of spontaneous emission quantum efficiency in GaAs/AlGaAs heterostructures grown by molecular beam epitaxy", Physica Status Solidi B (2007), pp. 2740-2751, vol. 244, Wiley-VCH, Berlin, Germany.

(Continued)

*Primary Examiner* — Marc Armand
*Assistant Examiner* — Felix Suarez

(57) ABSTRACT

Provided is a method and apparatus for measuring efficiency of an optical device. In the method, a power of emission light from the optical device is calculated by irradiating an excitation stimulus on the optical device. A power of a reference excitation stimulus at which a variation of recombination coefficients in a quantum well of the optical device with respect to a variation of carrier concentration in the quantum well of the optical device becomes minimum is extracted. An internal quantum efficiency of the optical device at the power of the reference excitation stimulus is calculated. An internal quantum efficiency of the optical device at powers of various excitation stimuli is calculated from the internal quantum efficiency of the optical device at the power of the reference excitation stimulus.

9 Claims, 9 Drawing Sheets

(56) References Cited

OTHER PUBLICATIONS

Y. J. Ding, et al., "Characterization of recombination processes in multiple narrow asymmetric coupled quantum wells based on the dependence of photoluminescence on laser intensity", Applied Physics Letters (Apr. 1992), pp. 2051-2053, vol. 60, American Institute of Physics, United States.

Y. Kawakami, et al., "Radiative and Nonradiative Recombination Processes in GaN-Based Semiconductors", Physica Status Solidi A (2001), pp. 41-50, vol. 183, Wiley-VCH, Berlin, Germany.

S. F. Chichibu, et al., "Recombination dynamics of localized excitons in cubic $InxGa1-xN$/GaN multiple quantum wells grown by radio frequency molecular beam epitaxy on 3C—SiC substrate" (Jul./Aug. 2003), Journal of Vacuum Science Technology B, pp. 1856-1862, vol. 21, American Vacuum Society, United States.

Shinji Saito, et al., "Estimation of internal quantum efficiency in InGaN-based light emitting diodes using electroluminescence decay times", Physica Status Solidi C (2008), pp. 2195-2197, vol. 5, Wiley-VCH, Berlin, Germany.

Hyungsung Kim, et al., "A Measurement Method of Internal Quantum Efficiency in InGaN-based Quantum Well Structure by Intensity Dependent Photoluminescence" (Oct. 2009), ICNS-8, pp. 514-515, vol. 1, ICC Jeju, Republic of Korea.

\* cited by examiner

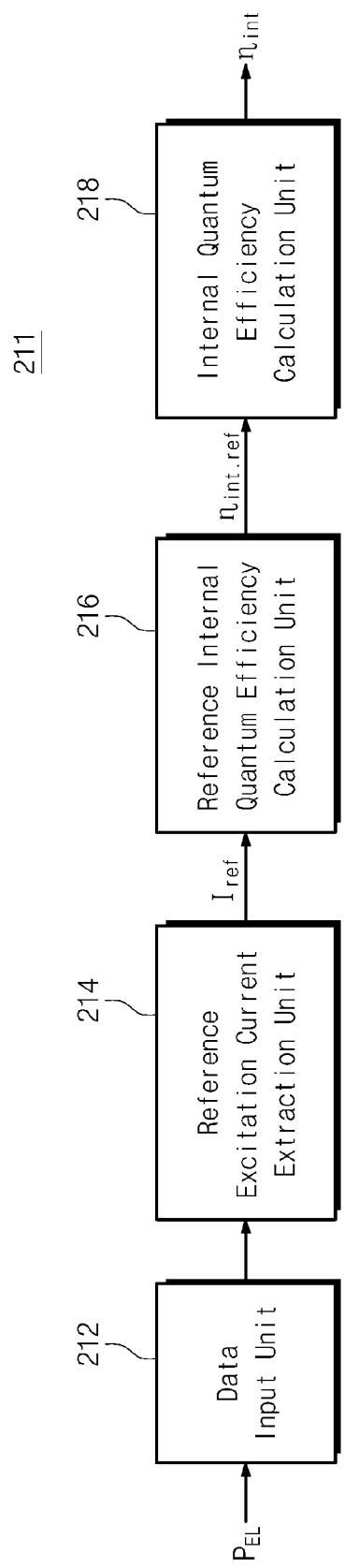

METHOD AND APPARATUS FOR MEASURING INTERNAL QUANTUM WELL EFFICIENCY OF LED

CROSS-REFERENCE TO RELATED APPLICATIONS

This U.S. non-provisional patent application claims priority under 35 U.S.C. §119 of Korean Patent Application No. 10-2010-0003836, filed on Jan. 15, 2010, the entire contents of which are hereby incorporated by reference.

BACKGROUND OF THE INVENTION

The present invention disclosed herein relates to an optical device, and more particularly, to a method and apparatus for measuring internal quantum efficiency of a light emitting diode (LED).

Generally, LEDs, which are being widely used as light sources, include the characteristics of small size, low power consumption, and high reliability. LEDs use chemical compounds such as AlGaAs, GaAlP, GaP, InGaAlP, and GaN. LEDs include an n-type semiconductor layer including chemical compounds, an active layer on the n-type semiconductor layer, and a p-type semiconductor layer on the active layer. LEDs, which are a sort of p-n junction diodes, are semiconductor devices using an electroluminescence effect in which monochromatic light is emitted when a forward voltage is applied. The wavelength of light emitted from an LED is determined by a bandgap energy (Eg) of a semiconductor being used.

SUMMARY OF THE INVENTION

The present invention provides a method and/or apparatus for measuring internal quantum efficiency of an LED.

Embodiments of the present invention provide methods for measuring efficiency of an optical device including: calculating a power of emission light from the optical device by irradiating an excitation stimulus on the optical device; extracting a power of a reference excitation stimulus at which a variation of recombination coefficients in a quantum well of the optical device with respect to a variation of carrier concentration in the quantum well of the optical device becomes minimum; calculating an internal quantum efficiency of the optical device at the power of the reference excitation stimulus; and calculating an internal quantum efficiency of the optical device at powers of various excitation stimuli from the internal quantum efficiency of the optical device at the power of the reference excitation stimulus.

In some embodiments, the excitation stimulus may be excitation light, the reference excitation stimulus may be reference excitation light, and the various excitation stimuli may be various excitation lights.

In other embodiments, the extracting of the power of the reference excitation stimulus may include extracting a power of reference excitation light at which a second order differential value of a second parameter (y) curve with respect to a first parameter (x) curve becomes minimum. The first parameter (x) may be $\sqrt{P_{PL}}$, and the second parameter (y) may be $P_L/\sqrt{P_{PL}}$. Here, the $P_L$ may be the power of the excitation light, and the $P_{PL}$ may be the power of the emission light.

In still other embodiments, the internal quantum efficiency of the optical device at the power of the reference excitation light may be $$\frac{\sqrt{P_{PL,ref}}}{\gamma_0 + \sqrt{P_{PL,ref}}}.$$

Here, $$\gamma_0 = \frac{(y_1 x_2 - y_2 x_1)}{y_2 - y_1}\bigg|_{\frac{\Delta y_1}{\Delta x_1} = \frac{\Delta y_2}{\Delta x_2}}.$$

$P_{PL,ref}$ may be the power of the reference emission light at the reference excitation light, and $x_1$, $x_2$, $y_1$, and $y_2$ may be physical quantities of the first parameter and the second parameter with respect to a small variation of the excitation light.

In even other embodiments, the internal quantum efficiency of the optical device at the powers of the various excitation lights may be $$\frac{\sqrt{P_{PL}}}{\gamma + \sqrt{P_{PL}}}.$$

Here, $\gamma$ may be $$\gamma^{2n+1} + x\gamma^{2n} - (\gamma_0 + x_0)\gamma_0^{2n}\frac{y}{y_0} = 0.$$

n may be a parameter according to a state of the optical device and a type of the excitation light.

In yet other embodiments, the internal quantum efficiency of the optical device at the powers of the various excitation lights may be $$\frac{\eta_{PL}(P_L)}{\eta_{PL}(P_{L,ref})}\eta_0.$$

Here, $\eta_{PL}$ may be spontaneous emission light efficiency and may be defined as $$\frac{P_{PL}/h\nu}{P_L/h\nu_L}.$$

$h\nu$ may be average photon energy of the natural emission light. $h\nu_L$ may be photon energy of the excitation light. $P_{L,ref}$ may be the power of the reference excitation light.

In further embodiments, the excitation stimulus may be excitation current. The reference excitation stimulus may be reference excitation current. The various excitation stimuli may be various excitation currents.

In still further embodiments, the extracting of the reference excitation current may include extracting a reference excitation current at which a second order differential value of a second parameter (y) curve with respect to a first parameter (x) becomes minimum. The first parameter (x) may be $\sqrt{P_{EL}}$, and the second parameter (y) may be $I/\sqrt{P_{EL}}$. Here, I may be the excitation current, and $P_{EL}$ may be the power of the emission light.

In even further embodiments, the internal quantum efficiency of the optical device at the reference excitation current may be $$\frac{\sqrt{P_{EL,ref}}}{\gamma_0 + \sqrt{P_{EL,ref}}}.$$

Here, $$\gamma_0 = \frac{(y_1 x_2 - y_2 x_1)}{y_2 - y_1}\bigg|_{\frac{\Delta y_1}{\Delta x_1} = \frac{\Delta y_2}{\Delta x_2}}.$$

$P_{EL,ref}$ may be the power of the reference emission light at the reference excitation current, and $x_1$, $x_2$, $y_1$, and $y_2$ may be physical quantities of the first parameter and the second parameter with respect to a small variation of the excitation current.

In yet further embodiments, the internal quantum efficiency of the optical device at the various excitation currents may be $$\frac{\sqrt{P_{EL,ref}}}{\gamma_0 + \sqrt{P_{EL,ref}}} \left(\frac{P_{EL}}{I}\right) \bigg/ \left(\frac{P_{EL,ref}}{I_{ref}}\right).$$

Here, $I_{ref}$ is the reference excitation current.

In other embodiments of the present invention, apparatuses for measuring efficiency of an optical device include: a light measurement unit measuring a power of emission light from the optical device by irradiating an excitation stimulus on the optical device; and an operation unit extracting a power of a reference excitation stimulus at which a variation of recombination coefficients in a quantum well of the optical device with respect to a variation of carrier concentration in the quantum well of the optical device becomes minimum, calculating an internal quantum efficiency of the optical device at the power of the reference excitation stimulus, and calculating an internal quantum efficiency of the optical device at powers of various excitation stimuli from the internal quantum efficiency of the optical device at the power of the reference excitation stimulus.

In some embodiments, the excitation stimulus may be excitation light or excitation current.

In still other embodiments of the present invention, computer-readable recording media storing a program to execute an optical device efficiency measurement method of any one of claims 1 to 10.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings:

FIG. 11 is a diagram illustrating an operation unit according to another embodiment of the present invention.

DETAILED DESCRIPTION OF PREFERRED EMBODIMENTS

Figure 1:
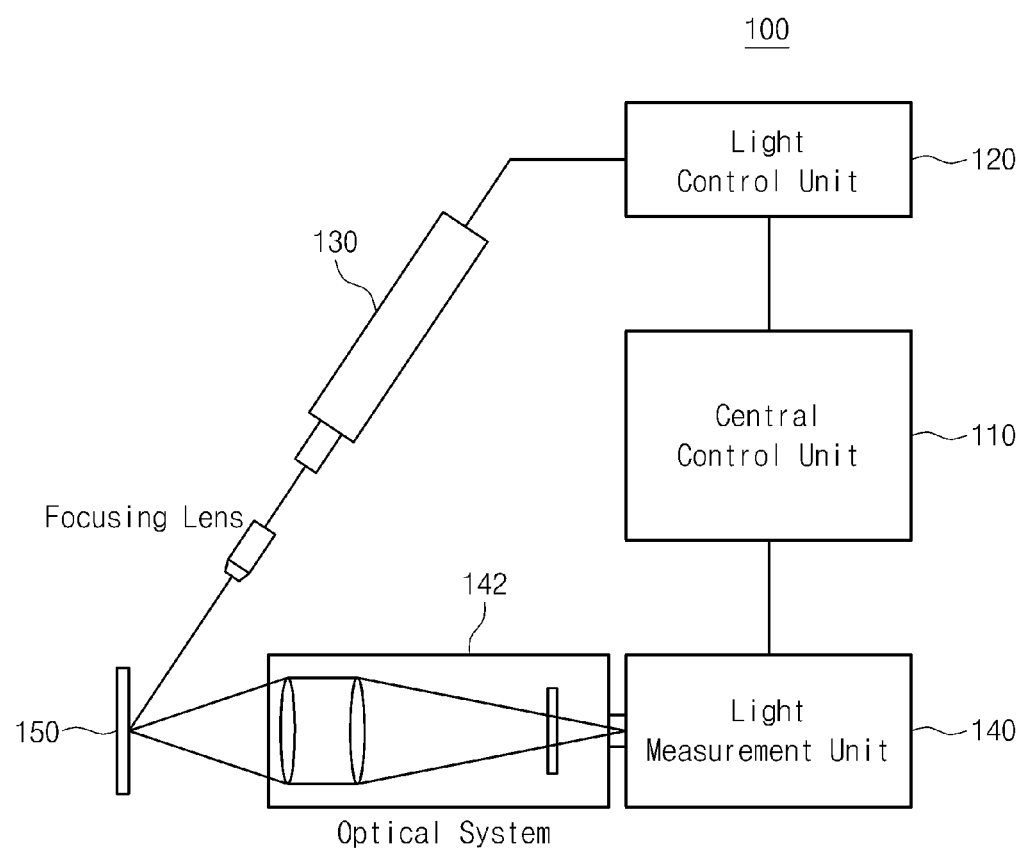
FIG. 1 is a diagram illustrating an optical device efficiency measurement apparatus according to an embodiment of the present invention.

Preferred embodiments of the present invention will be described below in more detail with reference to the accompanying drawings. The present invention may, however, be embodied in different forms and should not be constructed as limited to the embodiments set forth herein. Rather, these embodiments are provided so that this disclosure will be thorough and complete, and will fully convey the scope of the present invention to those skilled in the art.

The internal quantum efficiency of a light emitting diode (LED) may be improved through good crystal growth. The light extraction efficiency of the LED may be improved through a method of inserting various light scattering structures into the inside or surface of the LED.

Embodiments of the present invention may disclose a method for non-destructively measuring the internal quantum efficiency of an LED at a room or constant temperature. Embodiments of the present invention may be applied in a wafer, chip or chip on package state. Carriers of the LED may be excited, and lose energy in a form of emission light through recombination. Photoluminescence (PL) may occur s by irradiating light and electroluminescence (EL) may occur by injecting a current to optical devices. Generally, after an LED is formed on a wafer, photoluminescence may be measured in a wafer state, and electroluminescence may be measured in a chip or chip on package state.

Wall-plug efficiency, which is one of indicators representing the performance of an LED, may be expressed as Equation (1).

$$\eta_{wall\text{-}plug} = \frac{P_{out}}{VI} \qquad (1)$$

where $P_{out}$ is the power of emission light emitted from the LED to the outside, V is an applied voltage, and I is an injection current.

The above wall-plug efficiency $\eta_{wall\text{-}plug}$ of the LED may be expressed as Equation (2).

$$\eta_{wall\text{-}plug} = \frac{P_{out}}{VI} \quad (2)$$

$$= \left(\frac{n\overline{v}}{q(V_j + IR_s)}\right)\left(\frac{I_{active}/q}{I/q}\right)\left(\frac{P_{rad}/h\overline{v}}{I_{active}/q}\right)\left(\frac{P_{out}/h\overline{v}}{P_{rad}/h\overline{v}}\right)$$

$$= \eta_{voltage} \times \eta_{injection} \times \eta_{radiative} \times \eta_{extraction}$$

$$= \eta_{voltage} \times \eta_{internal} \times \eta_{extraction}$$

$$= \eta_{voltage} \times \eta_{external}$$

where $h\overline{v}$ is an average photon energy, $I_{active}$ is a current injected into a emission layer that is a Multiple Quantum Well (MQW), is $P_{rad}$ the power of light generated in the MQW, $P_{out}$ is the power of emission light emitted from the LED to the outside, $V_j$ is a voltage applied to a junction region of a p-n diode, and $R_s$ is a resistance generated in a portion except the junction region of the p-n diode. As shown in Equation (2), the wall-plug efficiency may be expressed as a production of a voltage efficiency $\eta_{voltage}$, an injection efficiency a $\eta_{injection}$, a radiative efficiency $\eta_{radiative}$, and an extraction efficiency $\eta_{extraction}$.

The voltage efficiency $\eta_{voltage}$ may represent a ratio of an average energy of an emitted photon to a potential energy of an electron injected into the LED. In an ideal case, the voltage efficiency $\eta_{voltage}$ equals 1, where the potential energy qV of one electron may be entirely changed into the one photon energy $h\overline{v}$. However, since the potential energy of an electron can be actually converted into heat energy due to a contact resistance of an electrode and a semiconductor, and a conductive resistance of a clad layer and a buffer layer, the voltage efficiency $\eta_{voltage}$ may be smaller than 1.

The injection efficiency $\eta_{injection}$ may represent a ratio of the number of carriers (current) injected into the emission layer to the number of carriers (current) injected into the LED. A portion of the injected carriers may be leaked to the clad layer or the buffer layer due to portions other than the active layer, for example, surface, wafer crack, and carrier overflow.

The electrons injected into the emission layer may have a potential energy obtained from the power source. A portion of the electrons injected into the active layer may be recombined with holes to lose their energy in a form of photon. The radiative efficiency $\eta_{radiative}$ may represent a ratio of the number of electrons losing their energy in a form of photons to the number of electrons injected into the active layer, and may be an important factor that determines the efficiency of the LED.

A portion of photons emitted from the active layer may be reabsorbed in the inside of the LED, and the other portion of photons may be emitted from the LED. The extraction efficiency $\eta_{extraction}$ may represent a ratio of the number of photons emitted from the LED to the number of photons generated in the emission layer.

The above-described efficiencies may be combined with each other to be expressed as other forms. The product of the injection efficiency $\eta_{injection}$ and the radiative efficiency $\eta_{radiative}$ may be defined as internal quantum efficiency $\eta_{internal}$, and may represent a ratio of the number of emitted photons to the number of injected electrons. Also, the product of the internal quantum efficiency $\eta_{internal}$ and the extraction efficiency n extraction may be defined as an external quantum efficiency $\eta_{external}$, and may be represent a ration of the number of photons emitted from the light emitting diode to the number of injected electrons.

The voltage efficiency $\eta_{voltage}$ and the external quantum efficiency $\eta_{external}$ may be experimentally obtained through a current-voltage characteristic curve of the LED, a current-optical output characteristic, and a spectrum measurement. On the other hand, a method for experimentally measuring the internal quantum efficiency $\eta_{internal}$ and the extraction efficiency $\eta_{extraction}$ that are very important for the performance of the LED is unknown.

When redefined using the concentration and life time of the carriers in the active layer, the internal quantum efficiency $\eta_{internal}$ may be expressed as Equation 3.

$$\eta_{internal}(T) = \frac{R_{rad}}{R_{rad} + R_{nrad}} = \frac{N/\tau_r}{N/\tau_r + N/\tau_{nr}} \quad (3)$$

$$R_{rad} = N/\tau_r = BN^2$$

$$R_{nrad} = N/\tau_{nr}$$

where N denotes the concentration of carriers (the number of carriers per unit volume) in the active layer.

It will be assumed that the number of electrons is equal to the number of holes. $R_{rad}$ and $R_{nrad}$, which are respectively the numbers of excited carriers of the emission layer disappearing by radiative recombination and non-radiative recombination per hour, may be defined as radiative recombination rate and non-radiative recombination rate, respectively. $\tau_r$ and $\tau_{nr}$, which are average life times of carriers disappearing by the radiative recombination and non-radiative recombination, may be defined as carrier lifetimes.

External quantum efficiency $\eta_{external}$ may be expressed as Equation (4) as defined in Equation (2).

$$\eta_{external} = \frac{P_{out}/h\overline{v}}{I/q} = \eta_{internal}\eta_{extraction} \quad (4)$$

The carrier rate equation in the quantum well of the LED may be expressed as the sum of the recombination rate R and the carrier generation rate G as shown in Equation (5).

$$\frac{dN}{dt} = -R + G \quad (5)$$

When the recombination rate R is expressed as a third order approximate function with respect to the carrier concentration, the recombination rate R may be expressed as Equation (6).

$$R = R_{nr} + R_r = (A + CN^2)N + BN^2 = \overline{A}N + BN^2 \quad (6)$$

where A, B and C are non-radiative recombination coefficient, radiative recombination coefficient, and Auger non-radiative recombination coefficient, respectively.

The carrier generation rate G may be expressed as Equations (7) and (8) according to a method of using optical excitation and a current injection method, respectively.

$$G_{opt} = \frac{1-R}{h v_L A_L} \alpha P_L \quad (7)$$

$$G_{cur} = \frac{\eta_{inj}}{qV_a} I \quad (8)$$

where R, $hv_L$, $A_L$, $\alpha$, $\eta_{inj}$, q, and $V_a$ are surface reflection rate, photon energy of excitation light, irradiation area, absorption coefficient, current injection efficient, elementary charge, and volume of the active layer, respectively. $P_L$[W] and I[A] are the powers of excitation light and current that are applied to the LED, respectively.

When electron-hole pairs are recombined due to injection of carriers into the active layer, emission light may be generated. Since the power of the emission light $P_{rad}$ from the active region is proportional to the radiative recombination rate, $P_{det}$ of the emission light actually measurable may be expressed as Equation (9).

$$P_{det} = (h\bar{v}\eta_{det}\eta_{extraction}V_a)BN^2 = \eta_c BN^2 \qquad (9)$$

where $\eta_{det}$ is the detector combination efficiency, and $\eta_{extraction}$ is the extraction efficiency that is defined as a ratio of the emission light emitted to the outside with respect to the emission light generated in the LED.

Equation (10) may be derived from Equation (5) and Equation (9).

$$\bar{A} + s\sqrt{P_{det}} = \eta_c s \frac{G}{\sqrt{P_{det}}} \qquad (10)$$

$$s = \sqrt{\frac{B}{\eta_c}}$$

Since the internal quantum efficiency $\eta_{internal}$ is a relative ratio of the radiative recombination rate to the total recombination rate, the internal quantum efficiency $\eta_{internal}$ may be expressed as Equation (11).

$$\eta_{int} = \frac{BN}{\bar{A}+BN} = \frac{s\sqrt{P_{det}}}{\bar{A}+s\sqrt{P_{det}}} \qquad (11)$$

Hereinafter, a relation between the variation of the carrier concentration and the radiative recombination coefficient will be described according to an embodiment of the present invention.

In an InGaN-based quantum well structure grown in a C-axis direction of a Wurtzeit structure, a strong internal electric field may exist. Accordingly, the energy band of an electron in the quantum well structure may have a sloped shape. However, if the carrier concentration in the quantum well of the emission layer increases, the internal electric field is offset by carriers, the energy band may have a flat shape. If the carrier concentration increases to such a degree that it offsets the internal electric field, the energy band of an electron may be flattened, and the transition probability of the electron between bands may gradually increase. That is, the radiative recombination coefficient B may increase according to the increase of the carrier concentration. On the other hand, when the carrier concentration is saturated by excessive injection of the carriers in a state where the energy band of the electron is flat, the carrier concentration may not increase anymore. In this case, the radiative recombination coefficient B may decrease according to momentum mismatch of electron-hole. The optical absorption coefficient α may decrease according to the carrier band filling phenomenon. The SRH recombination rate of the excited carrier concentration may be construed as a constant when it is greater than the intrinsic concentration and the concentration of traps existing in the band gap by a crystal defect.

Thus, when the carrier concentration in the quantum well is enough greater than the intrinsic concentration, and the energy band of an electron is flat, the recombination coefficients A, B and C in the quantum well of Equation (6) may have an unchangeable range with respect to the variation of the carrier concentration.

According to embodiments of the present invention, the power of the excitation light or the excitation current at which the recombination coefficients A, B and C are changed into the minimum values with respect to the carrier concentration in the quantum well can be obtained.

A method for measuring the internal quantum efficiency of an optical device according to an embodiment of the present invention will be described in detail. A method of using optical excitation will be described.

FIG. 1 is a diagram illustrating an optical device efficiency measurement apparatus 100 according to an embodiment of the present invention. Referring to FIG. 1, the optical device efficiency measurement apparatus 100 may include a central control unit 110, a light control unit 120, a light generation unit 130, and a light measurement unit 140. The optical device 150 may be a light emitting diode wafer or a light emitting diode chip.

The central control unit 110 may control the operation of the light measurement unit 140. The central control unit 110 may deliver a control signal to the light control unit 120 to allow excitation light from the light generation unit 130 to be irradiated on the optical device 150. The central control unit 110 may collect the power of emission light from the optical device 150 to calculate the efficiency of the optical device 150. The central control unit 110 may include an operation unit for calculating the efficiency of the optical device 150. The light generation unit 130 may include a laser. The light measurement unit 140 may obtain the emission light from the optical device 150 through an optical system 142. The light measurement unit 140 may exchange necessary data with the central control unit 110, and may generate an electrical signal corresponding to the power of the emission light from the optical device 150 to deliver it to the central control unit 110.

Hereinafter, a method (Power Dependent Photoluminescence; PDPL) of calculating the internal quantum efficiency of an optical device according to the variation of the power of excitation light in an operation unit will be described with reference to FIGS. 2 through 5.

As described above, when carriers are generated through optical excitation of a quantum well, a specific power of the excitation light at which the recombination coefficient A, B and C are changed into the minimum values may exist. Also, the characteristics of the absorption coefficient α may be proportional to the transition probability between bands. Accordingly, the absorption coefficient α may have properties similar to the radiative recombination coefficient B. Accordingly, the following Equation (12) can be assumed.

$$\alpha = K_{aB}(B)^n = K_{as}s^{2n} \qquad (12)$$

where $K_{aB}$ and $K_{as}$ are proportional coefficients, and n varies with the state of an LED and the type of excitation light.

Figure 2:
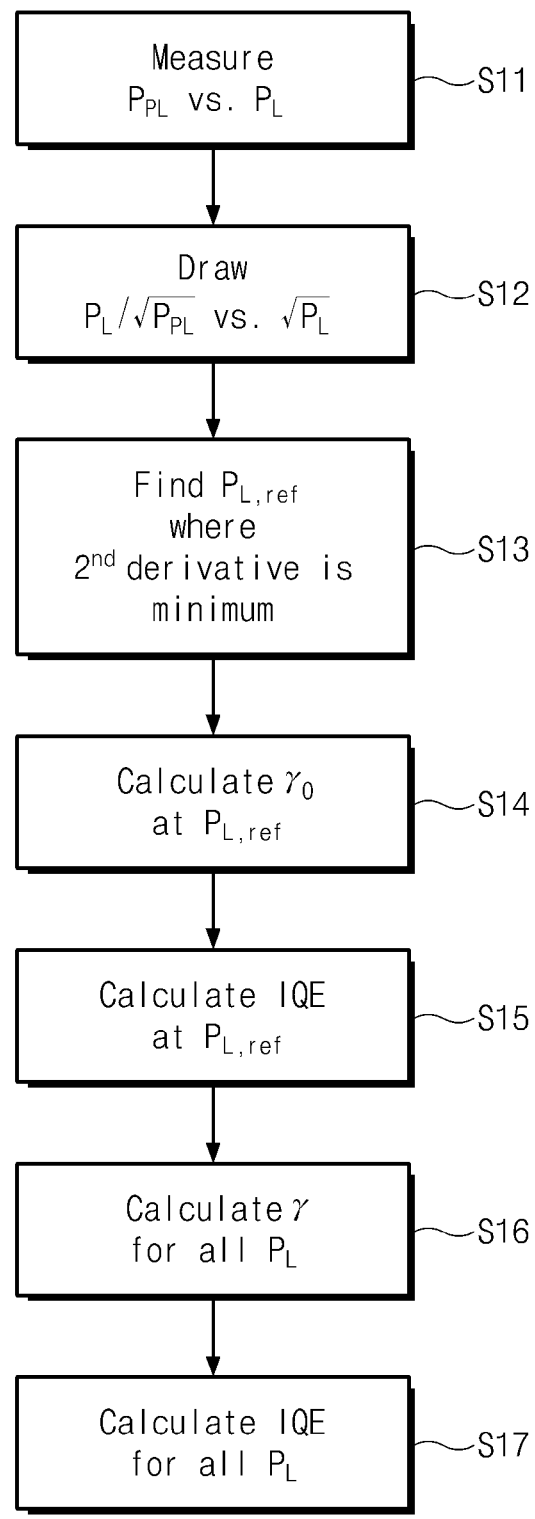
FIG. 2 is a flowchart illustrating a process for calculating internal quantum efficiency according to an embodiment of the present invention.
Figure 3:
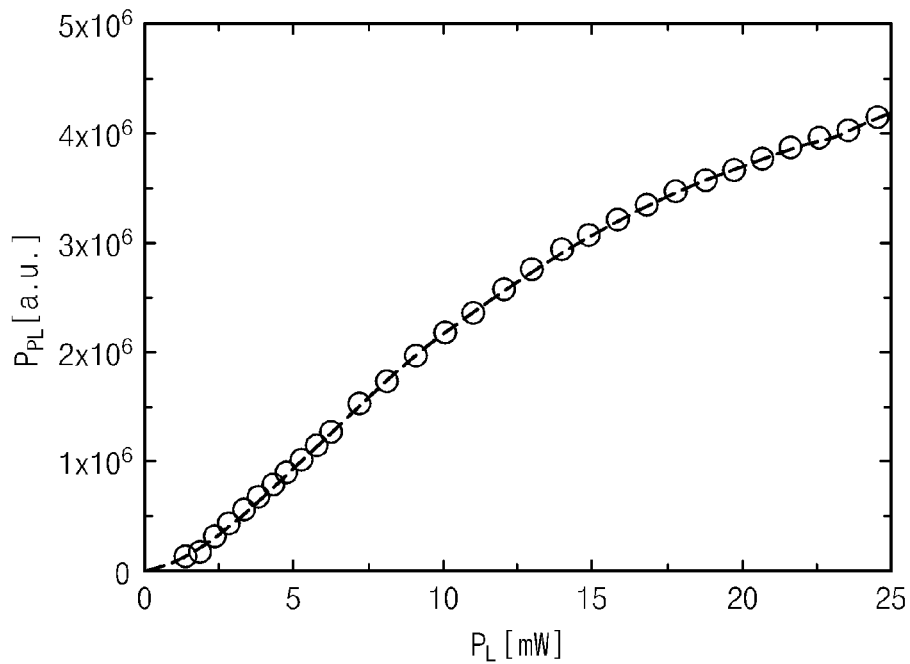
FIG. 3 is a graph illustrating an exemplary measurement of the power of emission light according to the power variation of excitation light.

Referring to FIGS. 2 and 3, with respect to the power $P_L$ of the excitation light used in exciting an active layer of the LED, the power $P_{PL}$, of emission light emitted to the outside from power of emission light generated by optical excitation is measured in operation S11. $P_{PL}$ is equal to the power $P_{det}$ of the emission light actually measured in Equations (9) through (11). When using the assumption of Equation (12), Equation (10) may be expressed as Equation (13).

$$\bar{A} + sx = ms^{2n+1}y \qquad (13)$$

$$m = \frac{1-R}{hv_L A_L}\eta_c,$$

$$x = \sqrt{P_{PL}},$$

$$y = \frac{P_L}{\sqrt{P_{PL}}}$$

where x may be named a first parameter, and y may be named a second parameter.

The internal quantum efficiency may be calculated at the power ($P_L = P_{L,ref}$) of reference excitation light. The power of the excitation light at which the variation of all recombination coefficients and the absorption coefficient with respect to the carrier concentration becomes minimum is $P_{L0}$, the condition of Equation (14) can be satisfied.

$$P_{L1}(=P_{L0}-\Delta P_L) < P_{L0} < P_{L2}(=P_{L0}+\Delta P_L), \Delta P_L << P_{L0} \quad (14)$$

where it will be assumed that the radiative recombination coefficient B is a constant, and a non-radiative recombination coefficient $\overline{A}$ is a variable. That is, B is a constant, and $\overline{A}$ is a function of the carrier concentration. In this case, the physical quantities A, s, x, and y may become $\overline{A}_0$, s0, x0, and y0 at the power $P_{L0}$ of the excitation light, respectively. When $\Delta \overline{A}$ values at the powers of the excitation light different from each other by a small variation $\Delta P_L$ based on the power $P_{L0}$ of the excitation light are equal to each other, Equation (13) may be expressed as Equations (15) through (17).

$$\overline{A}_0 + s_0 x_0 = m s_0^{2n+1} y_0 \quad (15)$$

$$(\overline{A}_0 + \Delta \overline{A}) + s_0(x_0 + \Delta x_1) = m s_0^{2n+1}(y + \Delta y_1) \quad (16)$$

$$(\overline{A}_0 + \Delta \overline{A}) + s_0(x_0 + \Delta x_2) = m s_0^{2n+1}(y + \Delta y_2) \quad (17)$$

where the subscripts 1 and 2 denote physical quantities regarding the small variation $\Delta P_L$.

The small variation $\Delta \overline{A}$ of the non-radiative recombination coefficient $\overline{A}$ with respect to the small variation of the power of the excitation light may be expressed as Equation (18).

$$\Delta \overline{A} = \frac{s_0(\Delta x_2 \Delta y_1 - \Delta x_1 \Delta y_2)}{y_2 - y_1} \quad (18)$$

Accordingly, Equation (19) has to be satisfied for a constant non-radiative recombination coefficient $\overline{A}$ at $P_{L1} < P_{L0} < P_{L2}$.

$$\frac{\Delta y_1}{\Delta x_1} = \frac{\Delta y_2}{\Delta x_2} \quad (19)$$

Accordingly, the gradients on a $P_L/\sqrt{P_{PL}}$ vs. $\sqrt{P_{PL}}$ curve have to be identical to each other with respect to the small variation $\Delta P_L$ of the power of the excitation light.

In contrast to the above description, the non-radiative recombination coefficient $\overline{A}$ may be a constant, and the radiative recombination coefficient B may be a function of the carrier concentration. When $\Delta s$ is the same with respect to the small variation $\Delta P_L$ of the power of the excitation light, Equations (20) through (22) may be satisfied.

$$\overline{A}_0 + s_0 x_0 = m s_0^{2n+1} y_0 \quad (20)$$

$$\overline{A}_0 + (s_0 + \Delta s)(x_0 + x_1) = m(s_0 + \Delta s)^{2n+1}(y + \Delta y_1) \quad (21)$$

$$\overline{A}_0 + (s_0 + \Delta s)(x_0 + \Delta x_2) = m(s_0 + \Delta s)^{2n+1}(y + \Delta y_2) \quad (22)$$

Accordingly, the variation $\Delta s$ of s may be expressed as Equation (23).

$$\frac{\Delta s}{s_0} = \frac{\Delta x_1 \Delta y_2 - \Delta x_2 \Delta y_1}{x_0 \Delta y_1 - x_0 \Delta y_2 + (2n+1)\Delta x_2 y_0 - (2n+1)\Delta x_1 y_0} \quad (23)$$

Accordingly, the condition in which $\Delta s(=\sqrt{\Delta B/\eta_c})$ representing the variation of the radiative recombination coefficient B becomes minimum and is treated as a constant may agree with Equation (19). Therefore, $P_{L0}$ satisfying Equation (19) may be defined as the power $P_{L,ref}$ of the reference excitation light.

Figure 4:
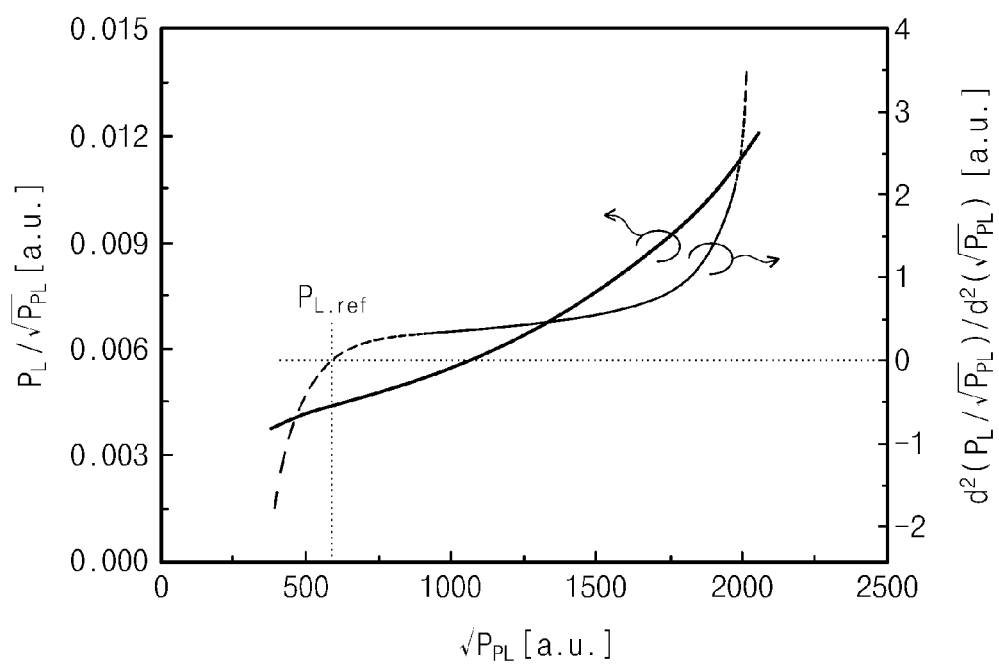
FIG. 4 is a graph illustrating a method for measuring the power of reference excitation light from a second parameter to a first parameter curve according to an embodiment of the present invention.

Referring to FIGS. 2 and 4, a graph of the second parameter y with respect to the first parameter x is drawn in operation S12. In the $P_L/\sqrt{P_{PL}}$ vs. $\sqrt{P_{PL}}$ curve, the power of the excitation light at a point where gradients are the same with respect to the small variation $\Delta P_L$ of the power of the excitation light may be defined as the power $P_{L,ref}$ of the reference excitation light. In other words, the power of the excitation light at which a 2nd order differential value of the second parameter y with respect to the first parameter x becomes minimum may be defined as the power $P_{L,ref}$ of the reference excitation light in operation S13.

Since $\overline{A} = \overline{A}_0$, and $s = s_0$ at the power $P_{L,ref}$ of the reference excitation light, Equation (24) may be satisfied with respect to the small variation $\Delta P_{L1}$ and $\Delta P_{L2}$ of the power of the excitation light.

$$\overline{A}_0 = \frac{(y_1 x_2 - y_2 x_1)}{y_2 - y_1} s_0 = \gamma_0 s_0 \quad (24)$$

Therefore, in operations S14 and S15, the internal quantum well efficiency (IQE) $\eta_{int,ref}$ at the power $P_{L,ref}$ of the reference excitation light may be finally expressed as Equation (25), by using Equations (11) and (24) that are the definition of the internal quantum well efficiency.

$$\eta_{int,ref} = \frac{s_0 \sqrt{P_{PL,ref}}}{\gamma_0 s_0 + s_0 \sqrt{P_{PL,ref}}} = \frac{\sqrt{P_{PL,ref}}}{\gamma_0 + \sqrt{P_{PL,ref}}} \quad (25)$$

where $$\gamma_0 = \frac{(y_1 x_2 - y_2 x_1)}{y_2 - y_1} \bigg|_{\frac{\Delta y_1}{\Delta x_1} = \frac{\Delta y_2}{\Delta x_2}}.$$

The internal quantum efficiency at a condition ($P_L \neq P_{L,ref}$) where the power $P_L$ of the excitation light is not the power $P_{L,ref}$ of the reference excitation light may be explained. A relation between s and the non-radiative recombination coefficient $\overline{A}$ with respect to the variation $\Delta P_L$ of the power of the excitation light may be expressed as Equation (26).

$$\overline{A} = \gamma s \quad (26)$$

All parameters of Equation (26) may be a function of the carrier concentration, i.e., a function of the power $P_L$ of the excitation light. The internal quantum well efficiency with respect to all powers of the excitation light except that $P_L = P_{L,ref}$ may be calculated in regard to the following two cases by using Equation (26). One is that the non-radiative recombination coefficient $\overline{A}$ is constant ($\overline{A} = \overline{A}_0$) with respect to all powers of the excitation light including the case where $P_L = P_{L,ref}$ and the other is that the radiative recombination coefficient B, i.e., s is a constant ($s = s_0$) with respect to all powers of the excitation light including the case where $P_L = P_{L,ref}$. Experimentally, the case where the non-radiative recombination coefficient $\overline{A}$ is a constant ($\overline{A} = \overline{A}_0$) is more appropriate, but two methods are all considered herein.

First, the case where the non-radiative recombination coefficient $\overline{A}$ is constant ($\overline{A}=\overline{A}_0$) with respect to the power of the excitation light will be described. Assuming that the non-radiative recombination coefficient $\overline{A}$ is constant with respect to all powers of the excitation light in Equation (26), a relation like Equation (27) may be established.

$$\frac{s}{s_0} = \frac{\gamma_0}{\gamma} = \sqrt{\frac{B}{B_0}} \tag{27}$$

Accordingly, by using Equation (20) in the case where $P_L = P_{L,ref}$ Equation (13) in the case where $P_L \neq P_{L,ref}$, and Equation (27), a proportional constant $\gamma$ may satisfy Equation (28).

$$\gamma^{2n+1} + x\gamma^{2n} - (\gamma_0 + x_0)\gamma_0^{2n}\frac{y}{y_0} = 0 \tag{28}$$

x and y may be experimentally-measured values, and $\gamma_0$ may be a value that can be obtained from Equation (25). Accordingly, $\gamma$ may be obtained from Equation (28) with respect to all powers $P_L$ of the excitation light at a random n in operation S16. On the other hand, the internal quantum well efficiency (IQE) with respect to all powers of the excitation light may be expressed as Equation (29) obtained from Equation (11). In operation S17, the internal quantum well efficiency (IQE) with respect to all powers of the excitation light can be obtained.

$$\eta_{int} = \frac{BN}{\overline{A}+BN} = \frac{\sqrt{P_{PL}}}{\gamma + \sqrt{P_{PL}}} \tag{29}$$

However, since calculated at a random n, $\gamma$ may not be exact. Another physical quantity has to be measured in order to obtain more exact $\gamma$. The other physical quantity may be carrier lifetime.

A relation among the radiative recombination lifetime $\tau_r$, radiative recombination coefficient B, and power of measured emission light $P_{PL}$ may be expressed as Equation (30), by using the second formula of Equation (3) and Equation (9).

$$\frac{BN}{B_o N_o} = \frac{\tau_{ro}}{\tau_r} = \frac{\gamma_0}{\gamma}\frac{\sqrt{P_{PL}}}{\sqrt{P_{PLo}}} \tag{30}$$

where 'o' denotes the physical quantity at $P_{L,ref}$.

Accordingly, when the radiative recombination lifetime $\tau_r$ is measured at the power $P_L$ of random excitation light using $\gamma_o$ from Equation (25), more exact $\gamma$ may be obtained. An unknown quantity n may be additionally obtained through numerical analysis using the obtained $\gamma$.

On the other hand, in regard to specific n values (e.g., n=0, 0.5, and 1), Equation (28) may be expressed as Equation (31), Equation (32), and Equation (33).

$$\gamma + x - (\gamma_0 + x_0)\frac{y}{y_0} = 0, \text{ for } n = 0 \tag{31}$$

$$\gamma^2 + x\gamma - (\gamma_0 + x_0)\gamma_0\frac{y}{y_0} = 0, \text{ for } n = 0.5 \tag{32}$$

$$\gamma^3 + x\gamma^2 - (\gamma_0 + x_0)\gamma_0^2\frac{y}{y_0} = 0, \text{ for } n = 1 \tag{33}$$

Since general values can be obtained from the above three cases, the internal quantum efficiency can be easily obtained without measuring other physical quantities.

On the other hand, the ratio $\eta_{PL}$ of spontaneous emission light efficiency may be defined as Equation (34).

$$\eta_{PL} = \frac{P_{PL}/h\overline{v}}{P_L/hv_L} \tag{34}$$

where $P_L$ is the power of the excitation light, $hv_L$ is photon energy of the excitation, $P_{PL}$ is the power of the measured emission light, and by is average photo energy of the emission light.

When n=0, the absorption coefficient of the excitation light may be treated as a constant based on Equation (12). The internal quantum efficiency may be expressed as Equation (35), by using the ratio $\eta_{PL}$ of the spontaneous emission light efficiency in Equation (34).

$$\eta_{int}(P_L) = \frac{\eta_{PL}(P_L)}{\eta_{PL}(P_{L,ref})}\eta_{int}(P_{L,ref}) \tag{35}$$

Hereinafter, the case where the radiative recombination coefficient is constant with respect to the power of the excitation light ($s=s_0$) will be described. When the radiative recombination coefficient is constant with respect to all powers of the excitation light in Equation (26), $\gamma$ may be expressed as Equation (36) with respect to the powers of the excitation light from Equation (13).

$$\gamma = (\gamma_0 + x_0)\frac{y}{y_0} - x \tag{36}$$

x and y may be experimentally-measured values, and $\gamma_0$ may be a value that can be obtained from Equation (25). Accordingly, $\gamma$ may be obtained from Equation (28) with respect to all powers of the excitation light. The internal quantum well efficiency with respect to all powers of the excitation light may be expressed as Equation (29) by using $\gamma$ obtained from Equation (36) and the measured value x.

Figure 5:
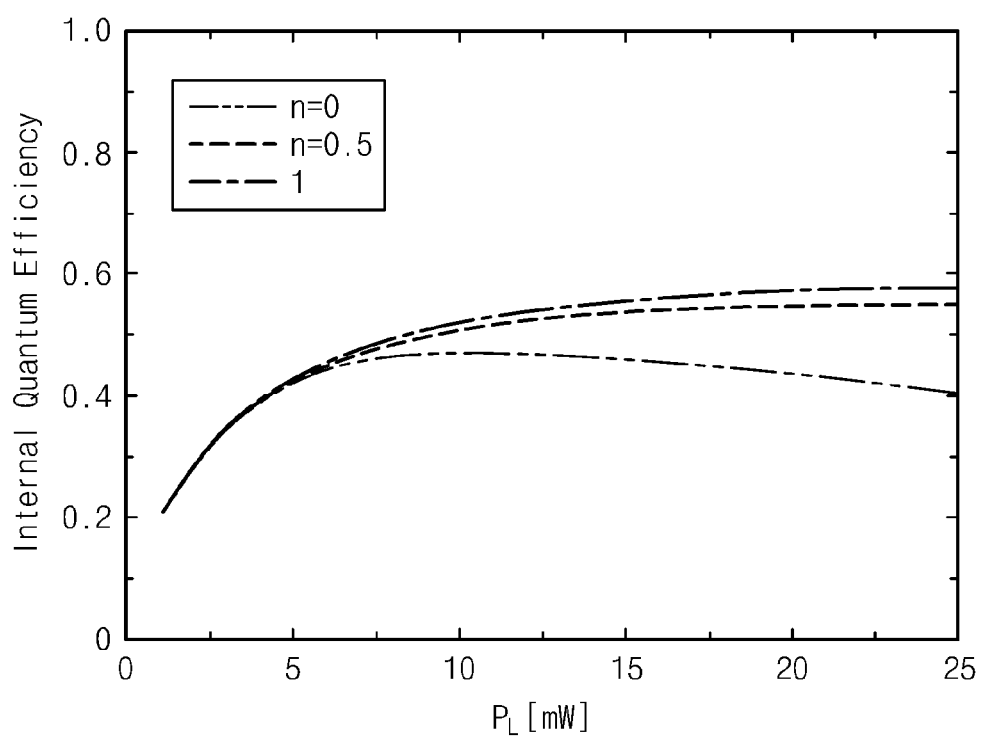
FIG. 5 is a graph illustrating the internal quantum efficiency obtained by analyzing the measurement result of FIG. 3 according to an embodiment of the present invention.

Referring to FIG. 5, a graph of the internal quantum efficiency with respect to various powers of the excitation light can be obtained by analysis of the measurement result of FIG. 3.

Figure 6:
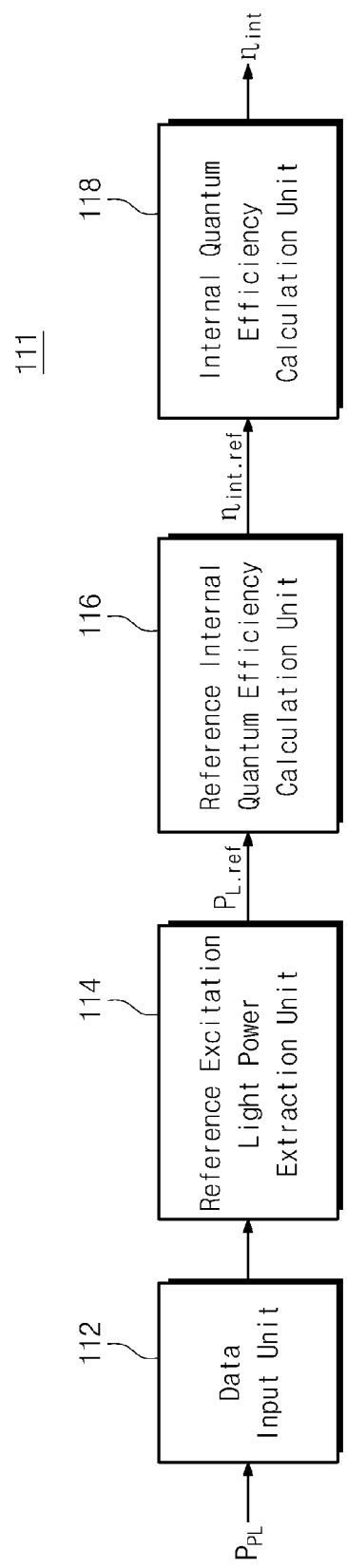
FIG. 6 is a diagram illustrating an operation unit according to an embodiment of the present invention.

Referring to FIG. 6, a process of calculating the optical device efficiency of the operation unit 111 constituting the central control unit 110 of the apparatus 100 of FIG. 1 will be described. The operation unit 111 according to an embodiment of the present invention may perform the above-described operations of FIG. 2. The operation unit 111 may include a data input unit 112, a reference excitation light power extraction unit 114, a temporary internal quantum efficiency calculation unit 116, and an internal quantum efficiency calculation unit 118.

The data input unit 112 may collect the power $P_{PL}$ of the emission light outputted from the light measurement unit 140 by unit of several nanoseconds. The reference excitation light power extraction unit 114 may extract the power $P_{L,ref}$ of the reference excitation light using Equations (14) through (23). The reference internal quantum efficiency calculation unit 116 may calculate the internal quantum efficiency $\eta_{int,ref}$ of the optical device at the power $P_{L,ref}$ of the reference excitation light using Equations (24) and (25). The internal quantum efficiency calculation unit 118 may calculate the internal quantum efficiency $\eta_{int}$ of the optical device at various powers of the excitation light using Equations (26) through (36).

Hereinafter, a method for measuring internal quantum efficiency of an optical device according to another embodiment of the present invention will be described in detail with reference to the accompanying drawings. A method for injecting a current will be described.

Figure 7:
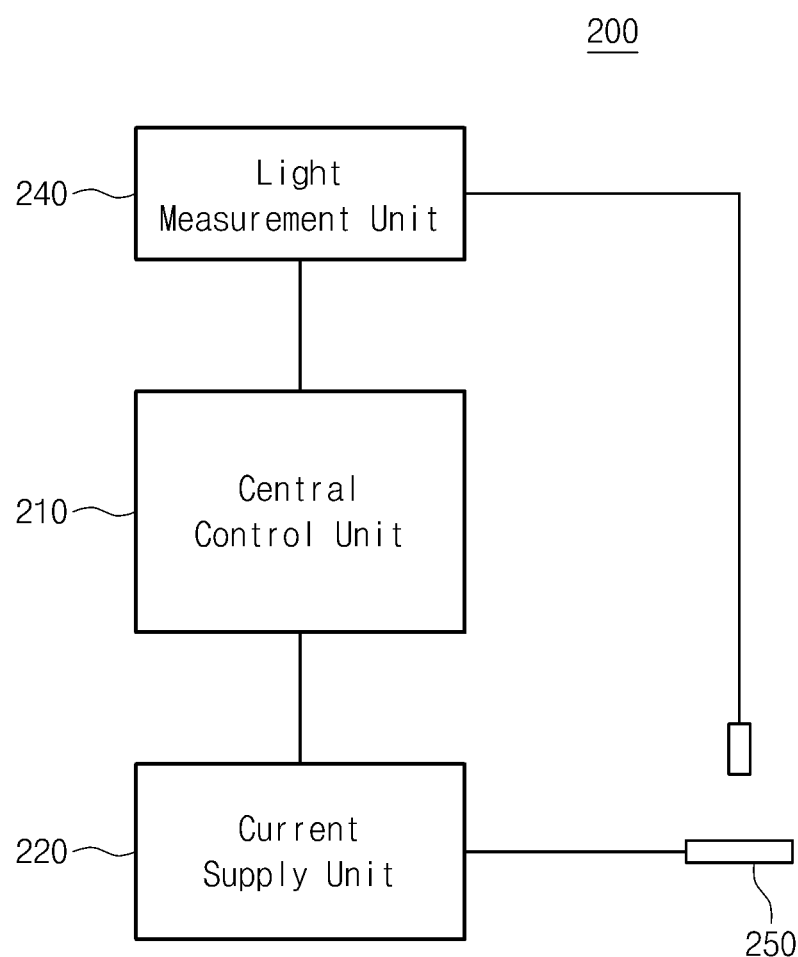
FIG. 7 is a diagram illustrating an optical device efficiency measurement apparatus according to another embodiment of the present invention.

FIG. 7 is a diagram illustrating an optical device efficiency measurement apparatus 200 according to another embodiment of the present invention. Referring to FIG. 7, the optical device efficiency measurement apparatus 200 may include a central control unit 210, a current supply unit 220 for applying an excitation current to an optical device 250, and a light measurement unit 240. The optical device 250 may be a light emitting diode wafer or a light emitting diode chip.

The central control unit 210 may control the operation of the light measurement unit 240. The central control unit 210 may collect the power of emission light from the optical device 250 to calculate the efficiency of the optical device 250, according to application of an excitation current via the current supply unit 220. The central control unit 210 may include an operation unit for calculating the efficiency of the optical device 250. The light measurement unit 240 may exchange necessary data with the central control unit 210. The central control unit 210 may deliver a control signal to the current supply unit 220 to inject a current having necessary power into the optical device 250. Also, the light measurement unit 240 may detect the emission light from the optical device 250 and generate a certain electrical signal corresponding to the power of the emission light to deliver it to the central control unit 210.

Hereinafter, a method (Current Dependent Electroluminescence; CDEL) of calculating the internal quantum efficiency of an optical device according to the variation of excitation current in an operation unit will be described with reference to FIGS. 8 through 10.

Figure 8:
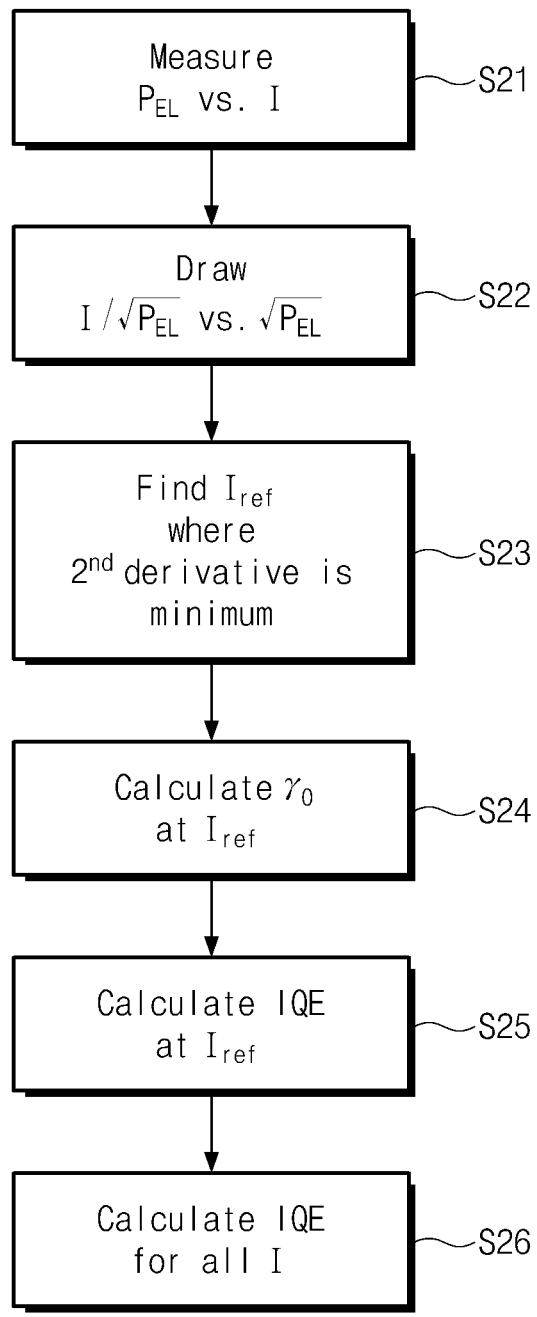
FIG. 8 is a flowchart illustrating a process for calculating internal quantum efficiency according to another embodiment of the present invention.
Figure 9:
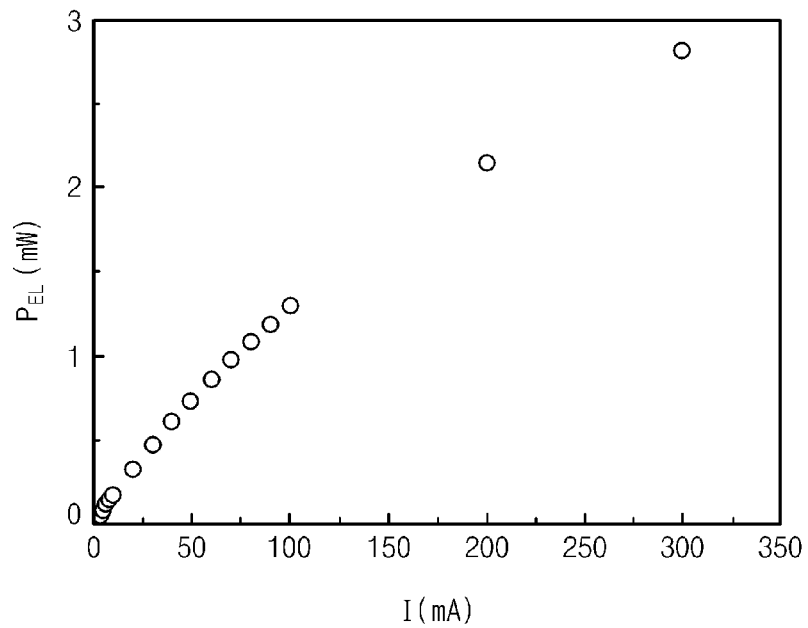
FIG. 9 is a graph illustrating an exemplary measurement of the power of emission light according to the variation of an excitation current.

Referring to FIGS. 8 and 9, the power $P_{EL}$ of emission light emitted to the outside may be measured from the power of emission light generated by the excitation current I in operation S21. Equation (10) may be expressed as Equations (37) through (39), by using Equations (8) and (9).

$$\overline{A} + sx = msy \tag{37}$$

$$m = \frac{\eta_{inj}}{qV_a}\eta_c \tag{38}$$

$$x = \sqrt{P_{EL}}, \quad y = \frac{I}{\sqrt{P_{EL}}} \tag{39}$$

where x may be named a first parameter, and y may be named a second parameter.

The internal quantum efficiency at reference excitation current (I=$I_{ref}$) will be described. The excitation current at which the variation of all recombination coefficients with respect to the carrier concentration becomes minimum is $I_0$, the following condition may be satisfied.

When $I_1(=I_0-\Delta I)<I_0<I_2(=I_0+\Delta I)$, $\Delta I \ll I_0$, B may be a constant, and non-radiative recombination coefficient $\overline{A}$ may vary. That is, B is a constant, and $\overline{A}$ may be a function of carrier concentration. In this case, the physical quantities A, s, x, and y may become $\overline{A}_0$, $s_0$, $x_0$ and $y_0$ at the excitation current $I_0$, respectively. When $\Delta \overline{A}$ values at the excitation current different from each other by a small variation $\Delta I$ based on the excitation current $I_0$ are equal to each other, Equations (37) through (39) may be expressed as Equations (40) through (42).

$$\overline{A}_0 + s_0 x_0 = m s_0 y_0 \tag{40}$$

$$(\overline{A}_0 + \Delta \overline{A}) + s_0(x_0 + \Delta x_1) = m s_0 (y + \Delta y_1) \tag{41}$$

$$(\overline{A}_0 + \Delta \overline{A}) + s_0(x_0 + \Delta x_2) = m s_0 (y + \Delta y_2) \tag{42}$$

where the subscripts 1 and 2 denote physical quantities regarding the small variation $\Delta I$.

The small variation $\Delta \overline{A}$ of the non-radiative recombination coefficient $\overline{A}$ with respect to the small variation $\Delta I$ of the excitation current may be expressed as Equation (43).

$$\Delta \overline{A} = \frac{s_0(\Delta x_2 \Delta y_1 - \Delta x_1 \Delta y_2)}{y_2 - y_1} \tag{43}$$

Accordingly, Equation (44) has to be satisfied for a constant non-radiative recombination coefficient $\overline{A}$ at $I_1 < I_0 < I_2$.

$$\frac{\Delta y_1}{\Delta x_1} = \frac{\Delta y_2}{\Delta x_2} \tag{44}$$

This is the substantially same result as the case where the excitation light is used. Accordingly, the gradients on a $I/\sqrt{P_{EL}}$ vs. $\sqrt{P_{EL}}$ curve have to be identical to each other with respect to the small variation $\Delta I_1$, $\Delta I_2$ of the excitation current.

In contrast to the above description, the non-radiative recombination coefficient $\overline{A}$ may be a constant, and the radiative recombination coefficient B may be a function of the carrier concentration. When $\Delta s$ is the same with respect to the small variation $\Delta I$ of the excitation current, Equations (45) through (47) may be satisfied.

$$\overline{A}_0 + s_0 x_0 = m s_0 y_0 \tag{45}$$

$$\overline{A}_0 + (s_0 + \Delta s)(x_0 + \Delta x_1) = m(s_0 + \Delta s)(y + \Delta y_1) \tag{46}$$

$$\overline{A}_0 + (s_0 + \Delta s)(x_0 + \Delta x_2) = m(s_0 + \Delta s)(y + \Delta y_2) \tag{47}$$

To mathematically summarize the above Equations, the variation $\Delta s$ of s with respect to the small variation $\Delta I$ of the excitation current may be expressed as Equation (48).

$$\frac{\Delta s}{s_0} = \frac{s_0(\Delta x_2 \Delta y_1 - \Delta x_1 \Delta y_2)}{x_0\{s_0(\Delta y_2 - \Delta y_1) + 3y_0(\Delta x_2 - \Delta x_1)\}} \tag{48}$$

Accordingly, the condition in which $\Delta s(=\sqrt{\Delta B/\eta_c})$ representing the variation of the radiative recombination coefficient B becomes minimum and is treated as a constant may agree with Equation (44). Therefore, $I_0$ satisfying Equation (44) may be defined as the reference excitation current $I_{ref}$.

Thus, a graph of the second parameter y with respect to the first parameter x is drawn in operation S22. In the $I/\sqrt{P_{EL}}$ vs. $\sqrt{P_{EL}}$ curve, the excitation current at a point where gradients are the same with respect to the small variation $\Delta I$ of the excitation current may be defined as the reference excitation current $I_{ref}$. In other words, the excitation current at which a 2nd order differential value of the second parameter y with respect to the first parameter x becomes minimum may be defined as the reference excitation current $I_{ref}$ in operation S23. Since $\overline{A}=\overline{A}_0$, and $s=s_0$ at the reference excitation current $I_{ref}$, Equation (49) may be satisfied.

$$\overline{A}_0 = \frac{(y_1 x_2 - y_2 x_1)}{y_2 - y_1} s_0 = \gamma_0 s_0 \qquad (49)$$

Therefore, in operations S24 and S25, the internal quantum well efficiency (IQE) $\eta_{int,ref}$ at the reference excitation current $I_{ref}$ may be finally expressed as Equation (50), by using Equations (11) and (49) that are the definition of the internal quantum well efficiency.

$$\eta_{int,ref} = \frac{s_0 \sqrt{P_{EL,ref}}}{\gamma_0 s_0 + s_0 \sqrt{P_{EL,ref}}} = \frac{\sqrt{P_{EL,ref}}}{\gamma_0 + \sqrt{P_{EL,ref}}} \qquad (50)$$

where $$\gamma_0 = \frac{(y_1 x_2 - y_2 x_1)}{y_2 - y_1}\bigg|_{\frac{\Delta y_1}{\Delta r_1} = \frac{\Delta r_2}{\Delta r_2}}.$$

The internal quantum efficiency at a condition $(I \neq I_{ref})$ where the excitation current I is not the reference excitation current $I_{ref}$ may be explained. The internal quantum efficiency with respect to all excitation current may be expressed as Equation (51), by using the definition of the external quantum efficiency of Equation (4).

$$\eta_{internal} = \frac{1}{\eta_{extraction}} = \frac{P_{EL}/h\overline{v}}{I/q} \qquad (51)$$

This is the same as the case where the reference injection current $I=I_{ref}$. Accordingly, when normalizing Equation (51) to $I=I_{ref}$, Equation (52) may be expressed.

$$\eta_{internal} = \eta_{internal,ref} \left(\frac{P_{EL}}{I}\right) \bigg/ \left(\frac{P_{EL,ref}}{I_{ref}}\right) \qquad (52)$$

In operation S26, since the right side of Equation (52) includes measurable physical quantities, the internal quantum well efficiency (IQE) may be obtained from all excitation current.

Figure 10:
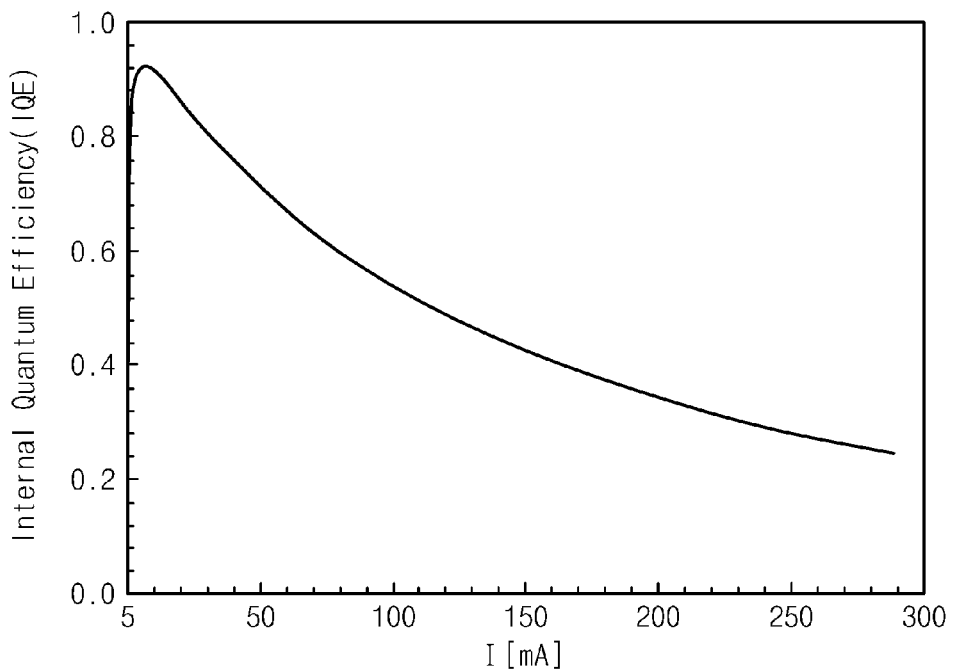
FIG. 10 is a graph illustrating the internal quantum efficiency obtained by analyzing the measurement result of FIG. 9 according to another embodiment of the present invention.

Referring to FIG. 10, a graph of the internal quantum efficiency with respect to various excitation current can be obtained by analysis of the measurement result of FIG. 9.

Referring to FIG. 11, calculating of the optical device efficiency of the operation unit 211 constituting the central control unit of FIG. 7 will be described. The operation unit 211 according to another embodiment of the present invention may perform the above-described operations of FIG. 8. The operation unit 211 may include a data input unit 212, a reference excitation current extraction unit 214, a temporary internal quantum efficiency calculation unit 216, and an internal quantum efficiency calculation unit 218.

The data input unit 212 may collect the power $P_{EL}$ of the emission light outputted from the light measurement unit 240 by unit of several nanoseconds. The reference excitation current extraction unit 214 may extract the reference excitation current $I_{ref}$ by using Equations (37) through (48). The reference internal quantum efficiency calculation unit 216 may calculate the internal quantum efficiency $\eta_{int,ref}$ of the optical device at the reference excitation current $I_{ref}$ by using Equations (49) and (50). The internal quantum efficiency calculation unit 218 may calculate the internal quantum efficiency $\eta_{int}$ of the optical device at various excitation current using Equations (51) and (52).

A relation among the external quantum well efficiency, the internal quantum well efficiency, and the light extraction efficiency has been described in Equation (2). The relation may be expressed as Equation (53).

$$\eta_{extraction} = \frac{\eta_{external}}{\eta_{internal}} \qquad (53)$$

Accordingly, the external quantum well efficiency $n_{external}$ may be an experimentally-measurable value, and the internal quantum well efficiency $\eta_{internal}$ may be a value extractable from the experimental result. Since two efficiencies may be obtained from all excitation currents, the light extraction efficiency $\eta_{extraction}$ can also be obtained. Since the emission spectrum and the applied voltage are known values, the voltage efficiency $\eta_{voltage}$ can also be calculated. Accordingly, the voltage efficiency $\eta_{voltage}$, the internal quantum well efficiency $\eta_{internal}$, and the light extraction efficiency $\eta_{extraction}$ can be separately measured.

In a method and apparatus for measuring the efficiency of an optical device according to the technical spirit of the present invention, the efficiency of a light emitting diode can be non-destructively measured through optical excitation or current injection at a normal or constant temperature. Directly after growth of an epitaxial thin film on a wafer, the efficiency of an LED can be measured using only the power data of emitting light, in all processing steps including a wafer state or a chip state.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A method for measuring efficiency of an optical device, comprising:
   calculating, by a light measurement unit, a power of emission light from the optical device by irradiating an excitation stimulus on the optical device;
   extracting, by an operation unit, a power of a reference excitation stimulus at which a variation of recombination coefficients in a quantum well of the optical device with respect to a variation of carrier concentration in the quantum well of the optical device becomes minimum;
   calculating, by the operation unit, an internal quantum efficiency of the optical device at the power of the reference excitation stimulus; and
   calculating, by the operation unit, an internal quantum efficiency of the optical device at powers of various excitation stimuli from the internal quantum efficiency of the optical device at the power of the reference excitation stimulus, wherein the excitation stimulus is excitation light, the reference excitation stimulus is reference excitation light, and the various excitation stimuli are various excitation lights, wherein the extracting of the power of the reference excitation stimulus comprises extracting a power of reference excitation light at which a second order differential value of a second parameter (y) curve with respect to a first parameter (x) curve becomes minimum, and the first parameter (x) is $\sqrt{P_{PL}}$, and the second parameter (y) is $P_L/\sqrt{P_{PL}}$, where the $P_L$ is the power of the excitation light, and the $P_{PL}$ is the power of the detected emission light.

2. The method of claim 1, wherein the internal quantum efficiency of the optical device at the power of the reference excitation light is $$\frac{\sqrt{P_{PL,ref}}}{\gamma_0 + \sqrt{P_{PL,ref}}},$$

where $$\gamma_0 = \frac{(y_1 x_2 - y_2 x_1)}{y_2 - y_1}\bigg|_{\frac{\Delta y_1}{\Delta r_1} = \frac{\Delta r_2}{\Delta r_2^2}},$$

$P_{PL,ref}$ is the power of the reference emission light at the reference excitation light, and $x_1$, $x_2$, $y_1$, and $y_2$ are physical quantities of the first parameter and the second parameter with respect to a small variation of the excitation light.

3. The method of claim 2, wherein the internal Quantum efficiency of the optical device at the powers of the various excitation lights is $$\frac{\sqrt{P_{PL}}}{\gamma + \sqrt{P_{PL}}},$$

where γ is $$\gamma^{2n+1} + x\gamma^{2n} - (\gamma_0 + x_0)\gamma_0^{2n}\frac{y}{y_0} = 0,$$

and n is a parameter according to a state of the optical device and a type of the excitation light.

4. The method of claim 2, wherein the internal quantum efficiency of the optical device at the powers of the various excitation lights is $$\frac{\eta_{PL}(P_L)}{\eta_{PL}(P_{L,ref})}\eta_0,$$

where $\eta_{PL}$ is spontaneous emission light efficiency and is defined as $$\frac{P_{PL}/h\nu}{P_L/h\nu_L},$$

hν is average photon energy of the natural emission light, $h\nu_L$ is photon energy of the excitation light, and $P_{L,ref}$ is the power of the reference excitation light.

5. A method for measuring efficiency of an optical device, comprising:

calculating, by a light measurement unit, a power of emission light from the optical device by irradiating an excitation stimulus on the optical device;

extracting, by an operation unit, a power of a reference excitation stimulus at which a variation of recombination coefficients in a quantum well of the optical device with respect to a variation of carrier concentration in the quantum well of the optical device becomes minimum;

calculating, by the operation unit, an internal quantum efficiency of the optical device at the power of the reference excitation stimulus; and calculating, by the operation unit, an internal quantum efficiency of the optical device at powers of various excitation stimuli from the internal quantum efficiency of the optical device at the power of the reference excitation stimulus, wherein the excitation stimulus is excitation current, the reference excitation stimulus is reference excitation current, and the various excitation stimuli are various excitation currents, wherein the extracting of the reference excitation current comprises extracting an reference excitation current at which a second order differential value of a second parameter (y) curve with respect to a first parameter (x) becomes minimum, and the first parameter (x) is $\sqrt{P_{EL}}$, and the second parameter (y) is $I/\sqrt{P_{EL}}$, where the I is the excitation current, and the $P_{EL}$ is the power of the emission light.

6. The method of claim 5, wherein the internal quantum efficiency of the optical device at the power of the reference excitation current is $$\frac{\sqrt{P_{EL,ref}}}{\gamma_0 + \sqrt{P_{EL,ref}}},$$

where $$\gamma_0 = \frac{(y_1 x_2 - y_2 x_1)}{y_2 - y_1}\bigg|_{\frac{\Delta y_1}{\Delta r_1} = \frac{\Delta r_2}{\Delta r_2^2}},$$

$P_{EL,ref}$ is the power of the reference emission light at the reference excitation current, and $x_1$, $x_2$, $y_1$, and $y_2$ are physical quantities of the first parameter and the second parameter with respect to a small variation of the excitation current.

7. The method of claim 6, wherein the internal quantum efficiency of the optical device at the various excitation currents is $$\frac{\sqrt{P_{EL,ref}}}{\gamma_0 + \sqrt{P_{EL,ref}}}\left(\frac{P_{EL}}{I}\right) \bigg/ \left(\frac{P_{EL,ref}}{I_{ref}}\right),$$

where $I_{ref}$ is the reference excitation current.

8. An apparatus for measuring efficiency of an optical device, comprising:
- a light measurement unit configured to measure a power of emission light from the optical device by irradiating an excitation stimulus on the optical device; and
- an operation unit configured to extract a power of a reference excitation stimulus at which a variation of recombination coefficients in a quantum well of the optical device with respect to a variation of carrier concentration in the quantum well of the optical device becomes minimum, to calculate an internal quantum efficiency of the optical device at the power of the reference excitation stimulus, and to calculate an internal quantum efficiency of the optical device at powers of various excitation stimuli from the internal quantum efficiency of the optical device at the power of the reference excitation stimulus,
- wherein the excitation stimulus is excitation light, the reference excitation stimulus is reference excitation light, and the various excitation stimuli are various excitation lights,
- wherein the operation unit is configured to extract the power of the reference excitation light at which a second order differential value of a second parameter (y) curve with respect to a first parameter (x) curve becomes minimum, and
- the first parameter (x) is $\sqrt{P_{EL}}$, and the second parameter (y) is $P_L/\sqrt{P_{PL}}$, where the $P_L$ is the power of the excitation light, and the $P_{PL}$ is the power of the detected emission light.

9. A non-transitory computer-readable recording medium storing a program containing instructions for causing a computer processor to:
- calculate, by a light measurement unit, a power of emission light from the optical device by irradiating an excitation stimulus on the optical device;
- extract, by an operation unit, a power of a reference excitation stimulus at which a variation of recombination coefficients in a quantum well of the optical device with respect to a variation of carrier concentration in the quantum well of the optical device becomes minimum;
- calculate, by the operation unit, an internal quantum efficiency of the optical device at the power of the reference excitation stimulus; and
- calculate, by the operation unit, an internal quantum efficiency of the optical device at powers of various excitation stimuli from the internal quantum efficiency of the optical device at the power of the reference excitation stimulus,
- wherein the excitation stimulus is excitation light, the reference excitation stimulus is reference excitation light, and the various excitation stimuli are various excitation lights,
- wherein the instructions to extract the power of the reference excitation stimulus comprises instructions to extract a power of reference excitation light at which a second order differential value of a second parameter (y) curve with respect to a first parameter (x) curve becomes minimum, and
- the first parameter (x) is $\sqrt{P_{PL}}$, and the second parameter (y) is $P_L/\sqrt{P_{PL}}$, where the $P_L$ is the power of the excitation light, and the $P_{PL}$ is the power of the detected emission light.

* * * * *